United States Patent
Upsher

[11] Patent Number: 5,906,576
[45] Date of Patent: May 25, 1999

[54] LIGHT COUPLING ASSEMBLY FOR USE IN A MEDICAL INSTRUMENT, SYSTEM AND METHOD

[75] Inventor: Michael Upsher, Los Angeles, Calif.

[73] Assignee: Mercury Enterprises, Inc., Clearwater, Fla.

[21] Appl. No.: 09/049,643

[22] Filed: Mar. 27, 1998

[51] Int. Cl.$^6$ .............................. A61B 1/06; F21V 29/00
[52] U.S. Cl. ........................ 600/178; 600/199; 362/294
[58] Field of Search .................................. 600/160, 178, 600/184, 185, 199, 245; 362/373, 294

[56] References Cited

U.S. PATENT DOCUMENTS

| | | |
|---|---|---|
| 4,337,761 | 7/1982 | Upsher . |
| 4,572,164 | 2/1986 | Yoshida et al. .......................... 600/178 |
| 5,076,660 | 12/1991 | Messinger ................................ 385/119 |
| 5,219,221 | 6/1993 | Yamaka et al. . |

FOREIGN PATENT DOCUMENTS

| | | | |
|---|---|---|---|
| 357204009 | 12/1982 | Japan ...................................... 600/178 |
| 91/11743 | 8/1991 | WIPO .................................... 600/178 |

*Primary Examiner*—Jeffrey A. Smith
*Attorney, Agent, or Firm*—Larson & Larson, P.A.; James E. Larson

[57] ABSTRACT

A light coupling assembly for use in providing light for illuminating an area of a patient's anatomy during the use of a medical instrument such as, for example, a laryngoscope is disclosed herein. The light coupling assembly includes a first light conveyance member having an input end for receiving light and an output end cooperating with the instrument in a way which illuminates the area with the light. A second light conveyance member includes an input end and an output end. The input end of the second member is positioned in optical communication with a source of light which also generates heat. A coupling arrangement is connected with the first and second members for positioning the input end of the first member in thermally isolated optical communication with the output end of the second member such that light from the first member is initially coupled to the second member in a way which prevents heat produced by the light source from damaging the first member. A system utilizing the light coupling assembly as one of its components and an associated method are also disclosed. The system provides for remote viewing of the illuminated anatomy of the patient on a monitor.

37 Claims, 2 Drawing Sheets

LIGHT COUPLING ASSEMBLY FOR USE IN A MEDICAL INSTRUMENT, SYSTEM AND METHOD

BACKGROUND OF THE INVENTION

The present invention relates generally to a light coupling assembly for use with medical instruments. More particularly, it relates to a light coupling assembly and associated system specifically configured to receive light from a remote source of light, which also generates heat, and to then direct this light to an instrument such as, for example, an endoscope such as a laryngoscope, through a fiber-optic cable in a way which prevents heat generated by the light source from damaging the fiber-optic cable.

Systems including a light source and associated equipment for coupling light from a light source to a medical instrument are known in the art. Typically, such systems utilize glass fiber-optic cable to couple the source light to the instrument and, thereafter, illuminate a particular area of a patient's anatomy. A medical practitioner can then view the illuminated area during a particular procedure by using a viewing arrangement such as a fiber-optic cable with an attached eyepiece. Such a prior art viewing arrangement is shown in U.S. Pat. No. 4,337,761, issued to the inventor of the present invention, in association with a laryngoscope so that an image of the illuminated area is provided at the eyepiece. In using such past systems, however, the subject anatomical area is generally rather dimly illuminated because relatively weak light sources are used, as these sources are typically powered by batteries housed, for example, in the handle of the instrument. More recently, external light sources have been provided. These sources typically couple light from a remote light source directly into a glass fiber-optic cable. However, illumination levels have not been dramatically improved by such external light sources. The relatively low light levels have been acceptable only because they are compensated for by the relatively sensitive eye of the practitioner directly viewing the image at the eyepiece.

Recent advances in the field of video imagery, including the availability of compact low cost CCD video cameras, have resulted in a fundamental change in the way practitioners may perform such procedures. It is now highly possible to directly couple a video camera to an eyepiece or other such arrangement whereby to allow a practitioner to view a procedure on a video monitor. This technique is advantageous for a number of reasons. For one, such a system is extremely useful in an instructional environment for training new practitioners. Trainees may be present for observation as the procedure is being performed or, alternatively, the procedure may be recorded for later viewing in a classroom environment. Additionally, a permanent video record of the procedure may prove to be useful for insurance and other purposes.

Unfortunately, the use of even the latest video camera requires relatively bright illumination of the patient's anatomy. It would seem that the simple expedient of increasing the brightness of the light source in the above described external source would resolve this problem. However, the light source also generates heat and a significantly brighter light source, which is suitable for use with a video camera, produces much more heat than former light sources which were used in conjunction with direct viewing by the human eye. In fact, the heat produced is increased to a level at which direct exposure damages plastic fiber-optic cables of this type which are desirable for use in this application. In prior art systems utilizing external light sources, such cables are positioned in close proximity with the light source to initially receive light for transmission to the instrument. This type of arrangement is not suitable for use with light sources contemplated for use with state of the art video viewing arrangements since the plastic fiber optic cable will ultimately be damaged by the generated heat of the light source. Substitution of other heat resistant light conductive materials such as, for example, glass or quartz in place of the plastic fiber-optic cable is also problematic. These alternate materials, while being less sensitive to heat, are also characterized by high internal light transmission losses. In addition, they are extremely expensive and have a tendency to break due to their multiple tiny fiber construction. Therefore, the use of these alternate materials, as a direct substitute for plastic fiber-optic cable, is self-defeating in that transmission losses are high enough that it becomes difficult to achieve acceptable illumination levels, without using very large composite bundles, and even when using the much brighter light sources contemplated by the present invention. It should be added that composite bundles have dead space between the fibers which significantly decrease their functional cross-section. This is not true of solid plastic fibers.

The present invention resolves the foregoing difficulties by providing a highly advantageous light coupling assembly which is adapted for use with an intense, heat producing light source and which couples this intense light to a low loss fiber-optic cable in a hybrid light path without subjecting the latter to damaging levels of heat produced by the light source; the cable can be made of a heat sensitive material, such as plastic, rendering the cable both light weight and disposable.

SUMMARY OF THE INVENTION

As will be described in more detail hereinafter, there is disclosed herein a light coupling assembly for use in providing light for illuminating an area of a patient's anatomy during the use of a medical instrument such as, for example, a laryngoscope. A system utilizing the light coupling assembly as one of its components and an associated method are also disclosed.

In accordance with the present invention, the light coupling assembly includes a first light conveyance member having an input end for receiving light and an output end cooperating with the instrument in a way which illuminates the area with the light. A second light conveyance member includes an input end and an output end. The input end of the second member is adapted for positioning in optical communication with a source of light which also generates large amounts of heat, generally speaking. The second member is constructed of a material which is less susceptible to the heat than the material from which the first member is constructed. A coupling arrangement is connected with the first and second members for positioning the input end of the first member in optical communication with the output end of the second member such that light from the first member is coupled to the second member and the first member is thermally isolated from the light source in a way which prevents heat produced by the light source from damaging the first member.

In a first feature, the coupling arrangement is in thermal communication with the second member to receive heat generated by the light source via the second member.

In a second feature, the coupling arrangement includes an integrally formed heat sink for dissipating heat received via the second member into the ambient environment.

A system for use in a medical procedure which requires illumination of an area of a patient's anatomy is also disclosed herein. The system includes an instrument adapted for performing the procedure and a light source which generates light and heat. A first light conveyance member includes an input end for receiving light and an output end cooperating with the instrument in a way which illuminates the area with the light. A second light conveyance member includes an input end and an output end. The input end of the second member is adapted for positioning in optical communication with the light source to initially receive this light. The second member is constructed of a material which is less susceptible to the heat than the material from which the first member is constructed. A coupling arrangement is connected with the first and second members for positioning the input end of the first member in optical communication with the output end of the second member such that light from the second member is coupled to the first member. The first member is thermally isolated from the light source in a way which prevents heat generated by the light source from damaging the first member.

In a first feature of the system, the instrument is a laryngoscope which includes a viewing arrangement for remotely viewing the illuminated area.

In a second feature of the system, the viewing arrangement includes a camera adapter. A video camera is mounted on the camera adapter. A monitor is connected to the camera such that an individual, who is operating the system, can remotely view the illuminated area on the monitor.

In a third feature of the system, the light source is positioned in an enclosure which supports the coupling arrangement such that the input end of the second member is in optical communication with the light source.

In a method of providing light for illuminating an area of a patient's anatomy in association with the use of a medical instrument such as, for example, a laryngoscope, light is produced remotely from the instrument by using a light source which also generates heat. A first light conveyance member is provided having an input end and an output end which cooperates with the instrument for illuminating the area with light. A second light conveyance member is provided having an input end and an output end such that the second member is formed from a material which is less susceptible to heat than the material from which the first member is formed. The input end of the second member is positioned in optical communication with the light source to initially receive the light and thereafter emit the light from its output end. The input end of the first member is positioned adjacent the output end of the second member such that light emitted from the second member is coupled to the input end of the first member in a way which thermally isolates the first member from the light source whereby to prevent the generated heat from damaging the first member.

In one preferred method, the coupling arrangement is provided in thermal communication with the second member to receive heat produced by the light source via the second member and, thereafter, dissipate the heat from the coupling arrangement into the ambient environment.

BRIEF DESCRIPTION OF THE DRAWINGS

The present invention may be understood by reference to the following detailed description taken in conjunction with the drawings, in which.

DETAILED DESCRIPTION OF THE INVENTION

Figure 1:
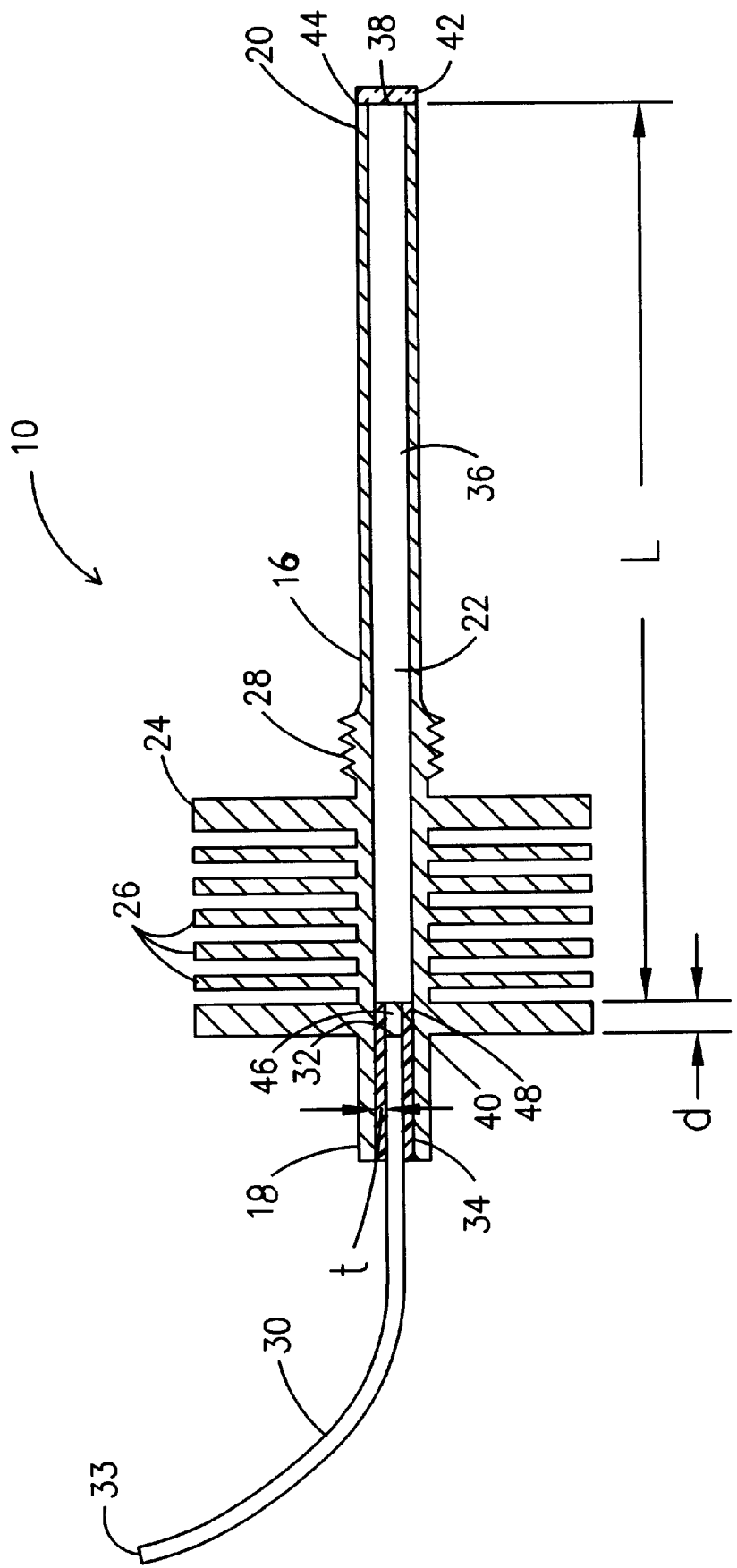
FIG. 1 is a cross-sectional elevational view of a light coupling assembly manufactured in accordance with the present invention for use in coupling relatively intense illuminating light to a medical instrument from a heat generating light source.

A light coupling assembly for use with a medical instrument and a system which utilizes the coupling assembly along with an associated method are disclosed herein. Attention is immediately directed to FIG. 1 which illustrates a light coupling assembly, generally indicated by reference number 10, manufactured in accordance with the present invention. Light coupling assembly 10 includes an elongated coupler 16 having opposing first and second ends 18 and 20, respectively, and defining a through-passage 22 therebetween. For purposes of simplicity of manufacture, through-passage 22 is generally formed having a circular cross-section (not shown), although other shapes are also suitable. Coupler 16 also includes an integrally formed circumferential heat sink 24 having a plurality of heat dissipating fins 26. A circumferential threaded flange 28 is also formed integrally with coupler 16 and is located adjacent to heat sink 24. The purposes of heat sink 24 and flange 28 will be described at appropriate points in the following discussion. Coupler 16 is formed from a heat conductive material such as, for example, aluminum or an aluminum alloy, although many other heat conductive materials may be used in accordance with the present invention.

Continuing to refer to FIG. 1, a first light conveyance member 30 includes an input end 32 and an output end 33. First member 30 is generally a circular cross-section plastic fiber-optic cable of the type which transmits light with very low losses and which is also typically damaged by exposure to heat at relatively low temperatures. As will be seen hereinafter, and in accordance with one feature of the present invention, the overall light coupling assembly is configured in a way which isolates first light conveyance member 30 from heat which can damage the member when the assembly is being used. To that end, input end 32 of cable 30 is captured within a heat isolator 34 having a wall thickness t. Heat isolator 34 is, in turn, captured within through-passage 22 at first end 18 of coupler 16. Heat isolator 34 and input end 32 may be retained in position by, for example, a friction fit or a suitable adhesive (not shown) and is cross-sectionally configured to conform to through-passage 22 and first member 30. Various materials can be used to form heat isolator 34 including ceramics which exhibit sufficiently low coefficients of thermal energy transfer. It is also anticipated that many other arrangements may be produced for retaining input end 32 of first light conveyance member 30 within coupler 16. For example, first end 18 of coupler 16 can be cooperatively configured with heat isolator 34 in a snap-fitting arrangement such that first member 30 and heat isolator 34 are readily removable to facilitate, for example, switching to a different instrument. These alternative arrangements are all considered to be within the scope of the invention.

A second light conveyance member 36 includes an input end 38, an output end 40 and a length L therebetween. Second member 36 is captured in through-passage 22 of coupler 16 such that input end 38 is flush with second end 20 of coupler 16 and the such that second member 36 is in thermal communication along its length L with coupler 16. To maximize thermal communication, second member 36 is generally configured as having the same cross-sectional shape, circular in the present example, as through-passage 22. Second light conveyance member 36 may be held in position within through-passage 22 by, for example, a friction fit, by heat conductive glue (not shown) which is also heat resistant or by any other arrangement (not shown) which maintains thermal communication between second member 36 and coupler 16. An infrared filter 42 is fixedly mounted on second end 20 of coupler 16 by, for example, a heat resistant adhesive 44 or by such items as mechanical fasteners (not shown) which extend through filter 42 and into coupler 16. Second light conveyance member 36 can be formed from a variety of heat resistant materials such as, for example, glass or quartz.

Still referring to FIG. 1, coupler 16 supports first and second light conveyance members, 30 and 36 respectively, such that input end 32 of first member 30 is in thermally isolated optical communication with output end 40 of second member 36 through a chamber 46 having a length d. Chamber 46 is cooperatively defined by input end 32 of first member 30, output end 40 of second member 36 and an end portion 48 of heat isolator 34. Chamber 46 may be evacuated, filled with air, or filled with a material such as a light transmissive, thermally isolating adhesive (not shown) such that first and second members, 30 and 36 respectively, remain in thermally isolated optical communication when the assembly is in use. With regard to length L of second member 36, two considerations govern. First, materials such as glass and quartz, from which second member 36 is formed, exhibit significant losses when used as conductors of light. Therefore, length L should be kept as short as possible in order to avoid unnecessary light attenuation. However, as a second consideration, it must be long enough to dissipate sufficient heat in order to protect first member 30. The significance of the foregoing design considerations, particularly with regard to thermal isolation, will become evident in conjunction with a discussion below of one overall system which uses light coupling assembly 10 in accordance with a method of the present invention.

Figure 2:
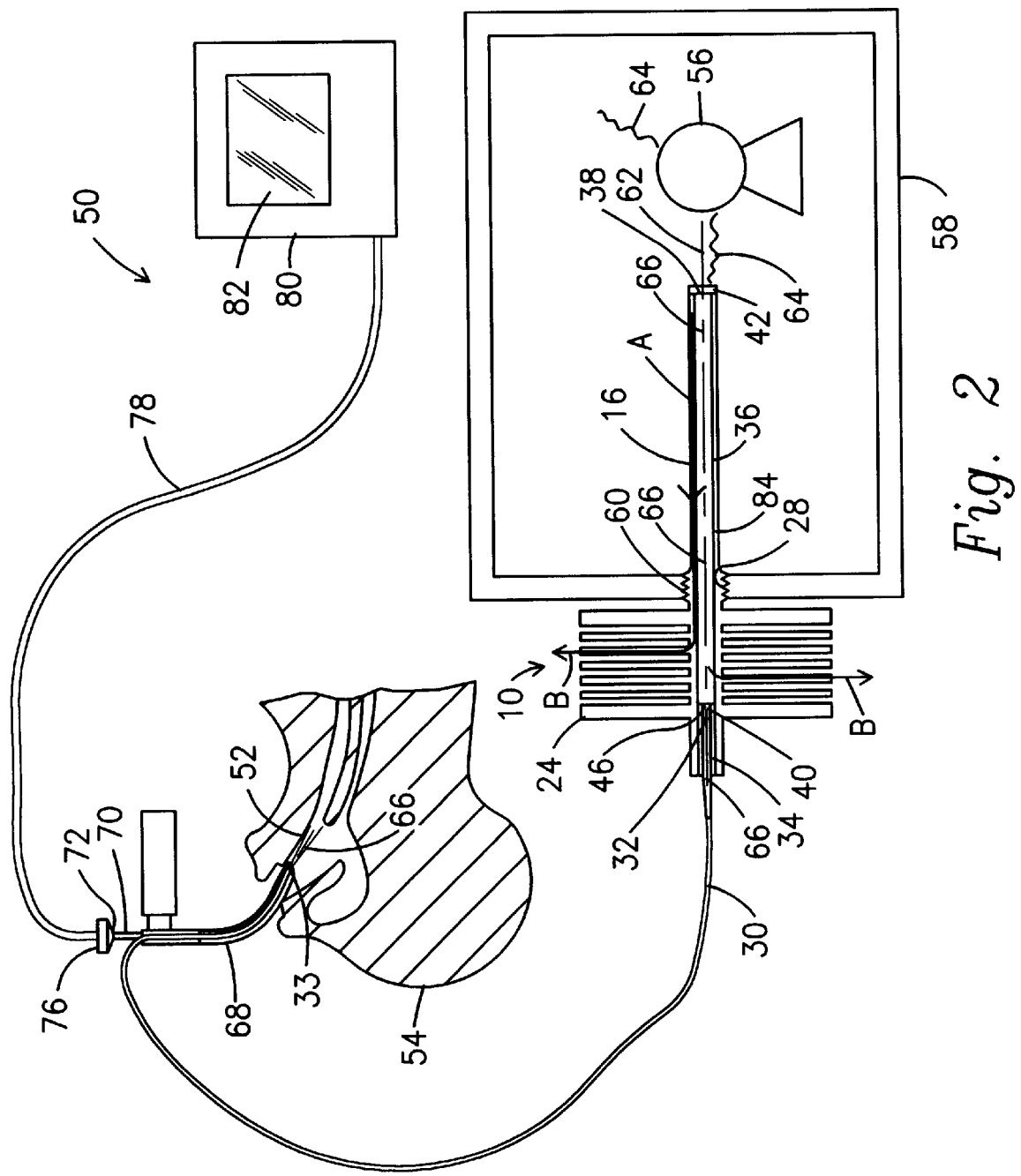
FIG. 2 illustrates the light coupling assembly of the present invention as part of an overall system for providing light to a medical instrument for illuminating a portion of a patient's anatomy using light which is produced by a light source within the system which also generates heat, and for remotely viewing the illuminated anatomy on a monitor screen.

Turning now to FIG. 2, light coupling assembly 10 is illustrated as forming part of an overall system 50 for use in a medical procedure which requires illumination of an area 52 of the anatomy of a patient 54. System 50 includes a light source 56 positioned within an enclosure 58. Flange 28 on light coupling assembly 10 is removably engaged in a threaded aperture 60 formed by enclosure 58, whereby to position infrared filter 42 in close proximity with light source 56 and to position heat sink 24 outside the enclosure and exposed to the ambient environment. Alternatively, flange 28 can be removably engaged to any one of a number of commercially available adapters (not shown) which will interface with their respective light sources. Light source 56 is a relatively intense emitter of light 62 and is also a significant source of heat 64. A variety of different types of sources are useful for providing light in the present application such as, for example, a Storz light source. Following emission, light 62 is incident upon infrared filter 42 of light coupling assembly 10. Filter 42 removes infrared components of emitted light 62 so as to permit a portion 66 of the light to be picked up by input end 38 of second light conveyance member 36. It is desirable to initially eliminate infrared components of light 62 using such a filter since these components can generate damaging heat at succeeding points within system 50. Infrared filter 42 can be formed from materials which are well known in the art.

Continuing to refer to FIG. 2, light 66 is conducted through second member 36 to be emitted at its output end. Light 66 is then coupled to input end 32 of first light conveyance member 30 through length d (see FIG. 1) of chamber 46. As previously mentioned, the chamber may be evacuated, contain air, or contain a thermally isolating material such as a suitable, optically-clear adhesive. After passing through chamber 46, light 66 is picked up by input end 32 or first light conveyance member 30 and then conducted by the latter to its output end 33. In the present example, output end 33 is attached directly to a laryngoscope 68 whereby light 66 is emitted from output end 33 to illuminate area 52 of the anatomy of patient 54 during an intubation procedure. However, it is to be understood that laryngoscope 68 is shown herein for illustrative purposes only, and that other instruments such as, for example, other types of endoscopes (not shown) may be used as part of the system of the present invention. Furthermore, it should also be appreciated that output end 33 of first member 30 may couple light to an instrument in many other ways. For instance, output end 33 may attach to the instrument in a way which couples light to a light input port provided on a handle or other portion of the instrument. The coupled light is then conducted by separately provided fiber-optic or other such elements which cooperate to receive the light and ultimately emit it onto the patient's anatomy.

Laryngoscope 68 further includes a viewing arrangement 70 for providing an image of illuminated area 52 at a camera adapter 72 through a viewing member 74 that is positioned on the laryngoscope. A compact video camera 76 is mounted on camera adapter 72 to produce a video signal which is thereafter transmitted through a cable 78 to a monitor 80. Monitor 80 includes a viewing screen 82 on which an image of the subject patient's anatomy is remotely reproduced from the video signal. It should also be mentioned that camera adapter 72 may be configured such that camera 76 can be removed therefrom and the image presented within the camera adapter can then be directly viewed by a practitioner, as with a prior art eyepiece.

Returning now to a discussion of thermal design considerations relevant to light coupling assembly 10, light source 56 is also a significant generator of heat 64, as previously noted. Infrared filter 42 and a portion 84 of coupler 16 are exposed either directly or indirectly to this heat within enclosure 58. Because coupler 16 is in thermal communication with second light conveyance member 36, heat 64 is also transferred thereto. In accordance with the present invention, light coupling assembly 10 is specifically configured so as to prevent first light conveyance member 30 from being damaged by heat 64.

Still referring to FIG. 2, protection of first member 30 from heat is accomplished in two significant ways by the arrangement of light coupling assembly 10. First, thermal isolation of first light conveyance member 30 from the overall assembly is provided. This isolation is accomplished through the use of heat isolator 34 in conjunction with chamber 46 whereby to thermally decouple the cable from the remaining assembly. Second, heat 64 is dissipated directly into the ambient environment and away from the first light conveyance member by coupler 16. Specifically, coupler 16, in being formed from aluminum, is an excellent thermal conductor. Heat 64, received by portion 84 of the coupler within enclosure 58, is conducted along a thermal path A (as indicated by arrows), directly to heat sink 24 for dissipation into the ambient surroundings by fins 26. Heat 64, received by second light conveyance member 36, is conducted along a thermal path B (also indicated by arrows) directly to heat sink 24 for dissipation therefrom, since second member 36 is in direct thermal communication with coupler 16. The combination of thermal isolation of first member 30 from heat 64 in conjunction with the ability of the overall light coupling assembly to dissipate the heat away from first member 30 along paths A and B, whereby to control the temperature of the overall assembly, results in exposure of input end 32 of first light conveyance member 30 to greatly reduced heat levels, even in the case where a bright, heat producing light source is used. Moreover, length L of second member 36 (see FIG. 1) is short enough to minimize attenuation of light passing through the member, yet long enough to ensure adequate dissipation of heat into heat sink 24 along path B.

The present invention advantageously provides for effectively coupling light produced by a brilliant, heat generating source to an instrument. The light is transferred to the instrument with low transmission losses along a hybrid light conducting path which initially includes a coupling assembly that is exposed to the heat and picks up light produced by the light source. Thereafter, the light is transferred by light coupling assembly 10 to a low loss fiber-optic cable without exposing the latter to unacceptable levels of heat such that an area of a patient's anatomy can be illuminated with light levels not previously seen in an external light source, remote viewing arrangement. The subject area is sufficiently illuminated for viewing using a video camera and associated monitor. An additional advantage resides in the fact that the light coupling assembly of the present invention is highly reliable since the assembly is constructed in a way which utilizes no moving parts.

It should also be mentioned that the light coupling assembly and associated system can be modified in a number of ways to suit specific applications based on, for example, heat generated by different types of light sources. For instance, in cases where a particularly hot light source is used, thermal isolation of first light conveyance member 30 can be further improved by increasing length d of chamber 46 and/or increasing thickness t of heat isolator 34. Still further improvement can be obtained by modifying the assembly to increase heat dissipation therefrom. This can be accomplished by, for example, increasing the number or size of fins 26 which make up heat sink 24.

Since the light coupling assembly and associated system disclosed herein may be modified in an unlimited number of ways, it should be understood that the present invention may be embodied in many other specific forms without departing from the spirit or scope of the present invention. Therefore, the present examples and methods are considered as illustrative and not restrictive, and the invention is not to be limited to the details given herein, but may be modified within the scope of the appended claims.

Having thus described the invention, what is claimed and desired to be secured by Letters Patent is:

1. A light coupling assembly for use in providing light for illuminating an area of a patient's anatomy during the use of a medical instrument such as, for example, a laryngoscope, said assembly comprising:

a) a first light conveyance member having an input end for receiving light and an output end cooperating with said instrument in a way which illuminates said area with said light, said first member being constructed of a first material;

b) a second light elongated conveyance member having an input end and an output end, said input end of said second member being adapted for positioning in optical communication with a source of said light which also generates heat, said second member being constructed of a second material which is less susceptible to said heat than said first material; and c) a coupling arrangement including an elongated coupler connected with the first and second members for positioning said input end of the first member in optical communication with the output end of the second member such that light from said first member is coupled to said second member and said first member is thermally isolated from said light source in a way which prevents said heat from damaging the first member.

2. A light coupling assembly in accordance with claim 1 wherein said coupling arrangement is in thermal communication with said second member to receive said generated heat via the second member.

3. A light coupling assembly in accordance with claim 2 wherein said coupling arrangement includes an integrally formed heat sink for dissipating said generated heat received by the coupling arrangement into the ambient environment.

4. A light coupling assembly in accordance with claim 3 wherein said heat sink and elongated coupler of said coupling arrangement which are in thermal communication with said second member are formed from a material consisting essentially of aluminum.

5. A light coupling assembly in accordance with claim 1 wherein said first member is an elongated plastic fiber-optic material.

6. A light coupling assembly in accordance with claim 1 wherein said second light elongated conveyance member is formed from quartz.

7. A light coupling assembly in accordance with claim 1 wherein said second light elongated conveyance member is formed from glass.

8. A light coupling assembly in accordance with claim 1 wherein said input end of said first member is positioned by said coupling arrangement in a way which thermally isolates the first member from the second member.

9. A light coupling assembly in accordance with claim 8 wherein said coupling arrangement includes a thermally isolating material which supports said input end of said first member to provide thermal isolation of said first member from said generated heat.

10. A light coupling assembly in accordance with claim 9 wherein said thermally isolating material is ceramic.

11. A light coupling assembly in accordance with claim 1 wherein said input end of said first member is separated from said output end of said second member by a chamber which is cooperatively defined by the first member, the second member and the coupling arrangement.

12. A light coupling assembly in accordance with claim 11 wherein said chamber is evacuated.

13. A light coupling assembly in accordance with claim 11 wherein said chamber is filled by air.

14. A light coupling assembly in accordance with claim 11 wherein said chamber is filled by a thermally isolating, light transmissive material.

15. A light coupling assembly in accordance with claim 14 wherein said material is glue.

16. A light coupling assembly in accordance with claim 1 wherein said input end of said second member includes an infrared filter positioned to prevent infrared components of said light from reaching said instrument.

17. A system for use in a medical procedure which requires illumination of an area of a patient's anatomy, said system comprising:

a) a light source which generates light and heat;

b) an instrument adapted for performing said procedure;

c) a first light conveyance member having an input end for receiving said light and an output end and cooperating with said instrument in a way which illuminates said area with said light, said first member being constructed of a first material;

d) a second light elongated conveyance member having an input end and an output end, said input end of said second member being adapted for positioning in optical communication with said light source to initially receive said light, said second member being constructed of a second material which is less susceptible to said heat than said first material; and e) a coupling arrangement including an elongated coupler connected with the first and second members for positioning said input end of the first member in optical communication with the output end of the second member such that light from said second member is coupled to said first member and said first member is thermally isolated from said light source in a way which prevents said heat from damaging the first member.

18. A system in accordance with claim 17 wherein said coupling arrangement is in thermal communication with said second member to receive said generated heat via the second member.

19. A system in accordance with claim 18 wherein said coupling arrangement includes an integrally formed heat sink for dissipating said generated heat into the ambient environment.

20. A system in accordance with claim 19 wherein said heat sink and elongated coupler of said coupling arrangement which are in thermal communication with said second member are formed from a material consisting essentially of aluminum.

21. A system in accordance with claim 17 wherein said first member is an elongated plastic fiber-optic material.

22. A system according to claim 17 wherein said instrument is a laryngoscope including a viewing arrangement for remotely viewing said illuminated area.

23. A system according to claim 22 wherein said viewing arrangement includes a camera adapter and wherein said system includes a video camera mounted on said camera adapter and a monitor connected to said camera such that an individual operating the system can remotely view said illuminated area on said monitor.

24. A system according to claim 17 including an enclosure in which said light source is positioned and wherein said coupling arrangement is supported by said enclosure such that said input end of said second member is in optical communication with the light source.

25. A system in accordance with claim 17 wherein said input end of said first member is positioned by said coupling arrangement in a way which thermally isolates the first member from the second member.

26. A system in accordance with claim 25 wherein said coupling arrangement includes a thermally isolating material which supports said input end of said first member to provide thermal isolation of said first member from said generated heat.

27. A system in accordance with claim 26 wherein said thermally isolating material is ceramic.

28. A system in accordance with claim 17 wherein said input end of said first member is separated from said output end of said second member by a chamber which is cooperatively defined by the first member, the second member and the coupling arrangement.

29. A system in accordance with claim 28 wherein said chamber is evacuated.

30. A system in accordance with claim 28 wherein said chamber is filled by air.

31. A system in accordance with claim 28 wherein said chamber is filled by a thermally isolating, light transmissive material.

32. A system in accordance with claim 31 wherein said material is glue.

33. A system in accordance with claim 17 wherein said second light conveyance member is formed from quartz.

34. A system in accordance with claim 17 wherein said second light conveyance member is formed from glass.

35. A system in accordance with claim 17 wherein said input end of said second member includes an infrared filter positioned to prevent infrared components of said light from reaching said instrument.

36. A method of providing light for illuminating an area of a patient's anatomy in association with the use of a medical instrument such as, for example, a laryngoscope, said method comprising the steps of:

a) producing light remotely from said instrument by using a light source which also generates heat;

b) providing a first light conveyance member having an input end and an output end, said output end cooperating with said instrument for illuminating said area with said light;

c) providing a second light elongated conveyance member having an input end and an output end, said second member being less susceptible to heat than said first member;

d) positioning said input end of said second member in optical communication with said light source to receive said light and thereafter emit the light from said output end; and e) positioning said input end of said first member adjacent said output end of said second member such that light emitted from said second member is coupled to the input end of the first member in a way which thermally isolates the first member from said light source whereby to prevent said generated heat from damaging the first member.

37. A method according to claim 36 including the steps of providing a coupling arrangement in thermal communication with said second member to receive said heat via the second member and thereafter, dissipating said heat from the coupling arrangement into the ambient environment.

* * * * *